US006743621B2

(12) United States Patent
Donoho et al.

(10) Patent No.: US 6,743,621 B2
(45) **Date of Patent: *Jun. 1, 2004**

(54) HUMAN PROTEASES AND POLYNUCLEOTIDES ENCODING THE SAME

(75) Inventors: Gregory Donoho, The Woodlands, TX (US); John Scoville, Houston, TX (US); C. Alexander Turner, Jr., The Woodlands, TX (US); Glenn Friedrich, Houston, TX (US); Alejandro Abuin, The Woodlands, TX (US); Brian Zambrowicz, The Woodlands, TX (US); Arthur T. Sands, The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/214,811

(22) Filed: Aug. 7, 2002

(65) Prior Publication Data

US 2003/0023062 A1 Jan. 30, 2003

Related U.S. Application Data

(63) Continuation of application No. 09/780,016, filed on Feb. 9, 2001, now Pat. No. 6,509,456.
(60) Provisional application No. 60/181,924, filed on Feb. 11, 2000.

(51) Int. Cl.[7] .......................... C12N 1/20; C12N 15/00; C12N 9/50; C07H 21/04
(52) U.S. Cl. ................. 435/252.3; 435/219; 435/320.1; 536/23.2
(58) Field of Search ........................... 435/252.3, 320.1, 435/219; 536/23.2

(56) References Cited

U.S. PATENT DOCUMENTS 4,215,051 A 7/1980 Schroeder et al.
4,376,110 A 3/1983 David et al.
4,594,595 A 6/1986 Struckman
4,631,211 A 12/1986 Houghten
4,689,405 A 8/1987 Frank et al.
4,713,326 A 12/1987 Dattagupta et al.
4,946,778 A 8/1990 Ladner et al.
5,252,743 A 10/1993 Barrett et al.
5,424,186 A 6/1995 Fodor et al.
5,445,934 A 8/1995 Fodor et al.
5,459,127 A 10/1995 Felgner et al.
5,556,752 A 9/1996 Lockhart et al.
5,656,603 A 8/1997 Simmons
5,700,637 A 12/1997 Southern
5,744,305 A 4/1998 Fodor et al.
5,869,336 A 2/1999 Meyer et al.
5,877,397 A 3/1999 Lonberg et al.
5,948,767 A 9/1999 Scheule et al.
5,972,680 A 10/1999 Knowles et al.
6,075,181 A 6/2000 Kucherlapati et al.
6,110,490 A 8/2000 Thierry
6,150,584 A 11/2000 Kucherlapati et al.

OTHER PUBLICATIONS

Bird et al, 1988, "Single–Chain Antigen–Binding Proteins", Science 242:423–426.

Bitter et al, "Expression and Secretion Vectors for Yeast", Methods in Enzymology 153:516–544.

Colbere–Garapin et al, 1981, "A New Dominant Hybrid Selective Marker for Higher Eukaryotic Cells", J. Mol. Biol. 150:1–14.

Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.

Greenspan et al, 1993, "Idiotypes: structure and immunogenicity", FASEB Journal 7:437–444.

Huse et al, 1989, "Generation of a Large Combinatorial Library of the Immunoglobulin Repertoire in Phage Lambda", Science 246:1275–1281.

Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.

Inoue et al., 1987, "Sequence–dependent hydrolysis of RNA using modified oligonucleotide splints and R Nase H", FEBS Letters 215(2):327–330.

Inoue et al, 1987, "Synthesis and hybridization studies on two complementary nona(2–'–O–methyl)ribonucleotides", Nucleic Acids Research 15(15):6131–6149.

Inouye & Inouye, 1985, "Up–promoter mutations in the lpp gene of *Escherichia coli*", Nucleic Acids Research 13(9):3101–3110.

Janknecht et al, 1991, "Rapid and efficient purification of native histidine–tagged protein expressed by recombinant vaccinia virus", PNAS 88:8972–8976.

Kohler & Milstein, 1975, "Continuous cultures of fused cells secreting antibody of predefined specificity", Nature 256:495–497.

Logan et al, 1984, "Adenovirus tripartite leader sequence enhances translation of mRNAs late after infection", Proc. Natl. Acad. Sci. USA 81:3655–3659.

Lowy et al. 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

(List continued on next page.)

*Primary Examiner*—P. Achutamurthy
*Assistant Examiner*—Yong D. Pak

(57) ABSTRACT

Novel human polynucleotide and polypeptide sequences are disclosed that can be used in therapeutic, diagnostic, and pharmacogenomic applications.

3 Claims, No Drawings

OTHER PUBLICATIONS

Mulligen & Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ripka, 1988, "Computers picture the perfect drug", New Scientist 16:54–57.

Ruther et al, 1983, "Easy identification of cDNA clones", EMBO Journal 2(10):1791–1794.

Santerre et al, 1994, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the Autographa californica Nuclear Polyhedosis Virus Genome: Deletion Mutations within the Polyhedrin Gene", J. Virol. 46(2):584–593.

Stein et al, 1988, "Physiochemical properties of phosphorothioate oligonucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Van Heeke et al, 1989, "Expression of Human Asparagine Synthetase in *Escherichia coli*", J. Biol. Chemistry 264(10):5503–5509.

Ward et al, 1989, "Binding activities of a repertoire single immunoglobulin variable domains secreted from *Escherichia coli*", Nature 341:544:546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci, USA 77(6):3567–3570.

Marra et al.: uj15h03.y1 Sugano mouse kidney mkia Mus musculus cDNA clone Image: 1908149 5' similar to SW:YEQ8_Yeast P40051 Hypothetical 58.0 KD Peptidase In ARG5,6–ILV1 Intergenic Region; mRNA sequence: EMBL Sequence Database, Oct. 31, 1998, XP 002171875.

Matthews, L: "Human DNA sequence from clone RP5–1057d18 on chromosome 22q13.33 Contains the gene for a novel protein similar to yeast and bacterial PEPP (aminopeptidase P, aminoacylproline aminopeptidase), ESTs and GSSs" EMBL Sequence Database, Feb. 24, 1999, XP002171876.

Collins et al.: "Novel human gene mapping to chromosome 22", EMBL Sequence Database, Jul. 12, 2000, XP002171877.

Collins et al.: "Hypothetical 58.0 kD protein" SWISSPROT Sequence Data Base, Oct. 1, 2000, XP00217878.

HUMAN PROTEASES AND POLYNUCLEOTIDES ENCODING THE SAME

The present application is a continuation of U.S. application Ser. No. 09/780,016, filed Feb. 9, 2001 now U.S. Pat. No. 6,509,456, which claims the benefit of U.S. Provisional Application No. 60/181,924 which was filed on Feb. 11, 2000, each of which are herein incorporated by reference in their entirety.

1. INTRODUCTION

The present invention relates to the discovery, identification, and characterization of novel human polynucleotides encoding proteins sharing sequence similarity with mammalian proteases. The invention encompasses the described polynucleotides, host cell expression systems, the encoded proteins, fusion proteins, polypeptides and peptides, antibodies to the encoded proteins and peptides, and genetically engineered animals that either lack or over express the disclosed sequences, antagonists and agonists of the proteins, and other compounds that modulate the expression or activity of the proteins encoded by the disclosed polynucleotides that can be used for diagnosis, drug screening, clinical trial monitoring, the treatment of physiological disorders or infectious disease.

2. BACKGROUND OF THE INVENTION

Proteases cleave protein substrates as part of degradation, maturation, and secretory pathways within the body. Proteases have been associated with, inter alia, regulating development, diabetes, obesity, infertility, modulating cellular processes, and infectious disease.

3. SUMMARY OF THE INVENTION

The present invention relates to the discovery, identification, and characterization of nucleotides that encode novel human proteins and the corresponding amino acid sequences of these proteins. The novel human proteins (NHPs) described for the first time herein share structural similarity with animal proteases, and particularly aminopeptidases.

The novel human nucleic acid (cDNA) sequences described herein, encode proteins/open reading frames (ORFs) of 507, 69, 290, 265, 211, 267, 186, 242, 453, 532, 428, 509, and 484 amino acids in length (see SEQ ID NOS: 2, 4, 6, 8, 10, 12, 14, 16, 18, 20, 22, 24, and 26 respectively).

The invention also encompasses agonists and antagonists of the described NHPs, including small molecules, large molecules, mutant NHPs, or portions thereof that compete with native NHPs, NHP peptides, and NHP antibodies, as well as nucleotide sequences that can be used to inhibit the expression of the described NHPs (e.g., antisense and ribozyme molecules, and gene or regulatory sequence replacement constructs) or to enhance the expression of the described NHPs (e.g., expression constructs that place the described sequence under the control of a strong promoter system), and transgenic animals that express a NHP transgene, or "knockout" animals (which can be conditional) that do not express a functional NHP. A gene trapped "knockout" murine ES cell line has been produced that mutates a murine homolog of the described NHPs. Accordingly, an additional aspect of the present invention includes a knockout mouse that is characterized by reduced levels of NHP expression.

Further, the present invention also relates to processes for identifying compounds that modulate, i.e., act as agonists or antagonists, of NHP expression and/or NHP activity that utilize purified preparations of the described NHP and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of the NHP ORFs encoding the described NHP amino acid sequences. SEQ ID NO:27 describes a NHP ORF with flanking sequences.

5. DETAILED DESCRIPTION OF THE INVENTION

The NHPs, described for the first time herein, are novel proteins that are expressed in, inter alia, human cell lines, and human fetal brain, brain, pituitary, cerebellum, spinal cord, thymus, spleen, lymph node, bone marrow, trachea, kidney, fetal liver, liver, prostate, testis, thyroid, adrenal gland, pancreas, salivary gland, stomach, small intestine, colon, uterus, placenta, mammary gland, adipose, skin, esophagus, bladder, cervix, rectum, pericardium, hypothalamus, ovary, fetal kidney, and fetal lung cells.

The described NHPs share sequence similarity with aminopeptidases, and particularly aminopeptidase P, from a variety of organisms. Aminopeptidases have been implicated in a variety cellular and disease processes and have been subject to considerable scientific scrutiny. For example, U.S. Pat. No. 5,972,680 describes uses and applications for proteases such as the presently described NHPs and U.S. Pat. No. 5,656,603 describes a variety of chemical antagonists of aminopeptidase P, both of which are herein incorporated by reference in their entirety.

The described sequences were compiled from gene trapped cDNAs and clones isolated from a human testis cDNA library (Edge Biosystems, Gaithersburg, Md.). The present invention encompasses the nucleotides presented in the Sequence Listing, host cells expressing such nucleotides, the expression products of such nucleotides, and: (a) nucleotides that encode mammalian homologs of the described sequences, including the specifically described NHPs, and the NHP products; (b) nucleotides that encode one or more portions of a NHP that correspond to functional domains of the NHP, and the polypeptide products specified by such nucleotide sequences, including but not limited to the novel regions of any active domain(s); (c) isolated nucleotides that encode mutant versions, engineered or naturally occurring, of a described NHP in which all or a part of at least one domain is deleted or altered, and the polypeptide products specified by such nucleotide sequences, including but not limited to soluble proteins and peptides in which all or a portion of the signal sequence is deleted; (d) nucleotides that encode chimeric fusion proteins containing all or a portion of a coding region of a NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF), or a contiguous exon splice junction first described in the Sequence Listing, that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants-of the disclosed NHP polynucleotide sequences.

Additionally contemplated are polynucleotides encoding a NHP ORF, or its functional equivalent, encoded by a polynucleotide sequence that is about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–27 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–27, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–27 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–27.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–27 provides detailed information about transcriptional changes involved in a specific pathway, potentially leading to the identification of novel components or gene functions that manifest themselves as novel phenotypes.

Probes consisting of sequences first disclosed in SEQ ID NOS:1–27 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–27 can be utilized in microarrays or other assay formats, to screen collections of genetic material from patients who have a particular medical condition. These investigations can also be carried out using the sequences first disclosed in SEQ ID NOS:1–27 in silico and by comparing previously collected genetic databases and the disclosed sequences using computer software known to those in the art.

Thus the sequences first disclosed in SEQ ID NOS:1–27 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–27. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relatve to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. *Acids Res.* 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215: 327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure, connective tissue disorders, infertility, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against normal NHP product, as described below. (For screening techniques, see, for example, Harlow, E. and Lane, eds., 1988, "Antibodies: A Laboratory Manual", Cold Spring Harbor Press, Cold Spring Harbor.)

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of a NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of a NHP in the body. The use of engineered host cells and/or animals may offer an advantage in that such systems allow not only for the identification of compounds that bind to the endogenous receptor for a NHP, but can also identify compounds that trigger NHP-mediated activities or pathways.

Finally, the NHP products can be used as therapeutics. For example, soluble derivatives such as NHP peptides/domains corresponding to NHP, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize an endogenous NHP receptor, accessory molecule, or substrate. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHP, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 THE NHP Sequences

The cDNA sequences and the corresponding deduced amino acid sequences of the described NHP are presented in the Sequence Listing. SEQ ID NO:27 describes a NHP ORF as well as flanking regions. The NHP nucleotides were obtained from human cDNA libraries using probes and/or primers generated from human gene trapped sequence tags. Expression analysis has provided evidence that the described NHPs are widely expressed in both human tissues as well as gene trapped human cells.

5.2 NHPs AND NHP Polypeptides

NHPs, NHP polypeptides, NHP peptide fragments, mutated, truncated, or deleted forms of NHP, and/or NHP fusion proteins can be prepared for a variety of uses. These uses include, but are not limited to, the generation of antibodies, as reagents in diagnostic assays, the identification of other cellular gene products related to a NHP, as reagents in assays for screening for compounds that can be as pharmaceutical reagents useful in the therapeutic treatment of mental, biological, or medical disorders and disease.

The Sequence Listing discloses the amino acid sequence encoded by the described NHP polynucleotides. The NHPs display initiator methionines in DNA sequence contexts consistent with a translation initiation site, and display a consensus signal sequence characteristic of secreted proteins.

The NHP amino acid sequences of the invention include the amino acid sequences presented in the Sequence Listing as well as analogues and derivatives thereof, as well as any oligopeptide sequence of at least about 10–40, generally about 12–35, or about 16–30 amino acids in length first disclosed in the Sequence Listing. Further, corresponding NHP homologues from other species are encompassed by the invention. In fact, any NHP encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions can be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, hreonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP products or NHP polypeptides are thought to be soluble or secreted molecules, the peptide or polypeptide can be recovered from the culture media. Such expression systems also encompass engineered host cells that express a NHP, or a functional equivalent, in situ. Purification or enrichment of NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP encoding nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. PGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign sequences. The virus grows in *Spodoptera frugiperda* cells. A NHP coding sequence can be cloned individually into non-essential regions (for example the polyhedrin gene) of the virus and placed under control of an ACNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in $tk^-$, $hgprt^-$ or $aprt^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in *Liposomes:A Practical Approach*, New, RRC ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHP to the target site or desired organ, where they cross the cell membrane and/or the nucleus where the NHP can exert its functional activity. This goal may be achieved by coupling of the NHP to a cytokine or other ligand that provides targeting specificity, and/or to a protein transducing domain (see generally U.S. applications Ser. Nos. 60/111, 701 and 60/056,713, both of which are herein incorporated by reference, for examples of such transducing sequences) to facilitate passage across cellular membranes and can optionally be engineered to include nuclear localization sequences.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in U.S. Pat. No. 6,150, 584 and respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP signaling pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. A recombinant expression vector comprising an isolated nucleic acid molecule that encodes the amino acid sequence shown in SEQ ID NO:2.

2. The recombinant expression vector of claim 1, wherein said isolated nucleic acid molecule comprises the nucleic acid sequence of SEQ ID NO:1.

3. A host cell comprising the vector of claim 1.

* * * * *

SEQUENCE LISTING

```
<160> NUMBER OF SEQ ID NOS: 27

<210> SEQ ID NO 1
<211> LENGTH: 1524
<212> TYPE: DNA
<213> ORGANISM: homo sapiens

<400> SEQUENCE: 1

atgccttggc tgctctcagc ccccaagctg gttcccgctg tagcaaacgt ccgcggcctc     60

tcaggatgta tgttgtgttc acagcgaagg tactcccttc agcctgtccc agaaaggagg    120

attccaaacc gatacttagg ccagcccagc ccctttacac acccacacct cctcagacca    180

ggggaggtaa ctccaggact atctcaggtg gaatatgcac ttcgcagaca caaactaatg    240

tctctgatcc agaaggaagc tcaagggcag agtgggacag accagacagt ggttgtgctc    300

tccaacccta catactacat gagcaacgat attccctata ctttccacca agacaacaat    360

ttcctgtacc tatgtggatt ccaagagcct gatagcattc ttgtccttca gagcctccct    420

ggcaaacaat taccatcaca caaagccata ctttttgtgc ctcggcgaga tcccagtcga    480

gaactttggg atggtccgcg atctggcact gatggagcaa tagctctaac tggagtagac    540

gaagcctata cgctagaaga atttcaacat cttctaccaa aaatgaaagc tgagacgaac    600

atggtttggt atgactggat gaggccctca catgcacagc ttcactctga ctatatgcag    660

cccctgactg aggccaaagc caagagcaag aacaaggttc ggggtgttca gcagctgata    720

cagcgcctcc ggctgatcaa gtctcctgca gaaattgaac gaatgcagat tgctgggaag    780

ctgacatcac aggctttcat agaaaccatg ttcaccagta aagcccctgt ggaagaagcc    840

tttctttatg ctaagtttga atttgaatgc cgggctcgtg gcgcagacat tttagcctat    900

ccacctgtgg tggctggtgg taatcggtca aacactttgc actatgtgaa aaataatcaa    960

ctcatcaagg atggggaaat ggtgcttctg gatggaggtt gtgagtcttc ctgctatgtg   1020

agtgacatca cacgtacgtg gccagtcaat ggcaggttca ccgcacctca ggcagaactc   1080

tatgaagccg ttctagagat ccaaagagat tgtttggccc tctgcttccc tgggacaagc   1140

ttggagaaca tctacagcat gatgctgacc ctgataggac agaagcttaa agacttgggg   1200

atcatgaaga acattaagga aaataatgcc ttcaaggctg ctcgaaaata ctgtcctcat   1260

catgttggcc actacctcgg gatggatgtc catgacactc cagacatgcc ccgttccctc   1320

cctctgcagc ctgggatggt aatcacaatt gagcccggca tttatattcc agaggatgac   1380

aaagatgccc cagagaagtt tcggggtctt ggtgtacgaa ttgaggatga tgtagtggtg   1440

actcaggact cacctctcat cctttctgca gactgtccca aagagatgaa tgacattgaa   1500

cagatatgca gccaggcttc ttga                                          1524

<210> SEQ ID NO 2
<211> LENGTH: 507
<212> TYPE: PRT
<213> ORGANISM: homo sapiens

<400> SEQUENCE: 2

Met Pro Trp Leu Leu Ser Ala Pro Lys Leu Val Pro Ala Val Ala Asn
 1               5                  10                  15

Val Arg Gly Leu Ser Gly Cys Met Leu Cys Ser Gln Arg Arg Tyr Ser
            20                  25                  30

Leu Gln Pro Val Pro Glu Arg Arg Ile Pro Asn Arg Tyr Leu Gly Gln
```

-continued

```
        35                  40                  45

Pro Ser Pro Phe Thr His Pro His Leu Leu Arg Pro Gly Glu Val Thr
    50                  55                  60

Pro Gly Leu Ser Gln Val Glu Tyr Ala Leu Arg Arg His Lys Leu Met
65                  70                  75                  80

Ser Leu Ile Gln Lys Glu Ala Gln Gly Gln Ser Gly Thr Asp Gln Thr
                85                  90                  95

Val Val Val Leu Ser Asn Pro Thr Tyr Tyr Met Ser Asn Asp Ile Pro
            100                 105                 110

Tyr Thr Phe His Gln Asp Asn Asn Phe Leu Tyr Leu Cys Gly Phe Gln
        115                 120                 125

Glu Pro Asp Ser Ile Leu Val Leu Gln Ser Leu Pro Gly Lys Gln Leu
    130                 135                 140

Pro Ser His Lys Ala Ile Leu Phe Val Pro Arg Arg Asp Pro Ser Arg
145                 150                 155                 160

Glu Leu Trp Asp Gly Pro Arg Ser Gly Thr Asp Gly Ala Ile Ala Leu
                165                 170                 175

Thr Gly Val Asp Glu Ala Tyr Thr Leu Glu Glu Phe Gln His Leu Leu
            180                 185                 190

Pro Lys Met Lys Ala Glu Thr Asn Met Val Trp Tyr Asp Trp Met Arg
        195                 200                 205

Pro Ser His Ala Gln Leu His Ser Asp Tyr Met Gln Pro Leu Thr Glu
    210                 215                 220

Ala Lys Ala Lys Ser Lys Asn Lys Val Arg Gly Val Gln Gln Leu Ile
225                 230                 235                 240

Gln Arg Leu Arg Leu Ile Lys Ser Pro Ala Glu Ile Glu Arg Met Gln
                245                 250                 255

Ile Ala Gly Lys Leu Thr Ser Gln Ala Phe Ile Glu Thr Met Phe Thr
            260                 265                 270

Ser Lys Ala Pro Val Glu Glu Ala Phe Leu Tyr Ala Lys Phe Glu Phe
        275                 280                 285

Glu Cys Arg Ala Arg Gly Ala Asp Ile Leu Ala Tyr Pro Pro Val Val
    290                 295                 300

Ala Gly Gly Asn Arg Ser Asn Thr Leu His Tyr Val Lys Asn Asn Gln
305                 310                 315                 320

Leu Ile Lys Asp Gly Glu Met Val Leu Leu Asp Gly Gly Cys Glu Ser
                325                 330                 335

Ser Cys Tyr Val Ser Asp Ile Thr Arg Thr Trp Pro Val Asn Gly Arg
            340                 345                 350

Phe Thr Ala Pro Gln Ala Glu Leu Tyr Glu Ala Val Leu Glu Ile Gln
        355                 360                 365

Arg Asp Cys Leu Ala Leu Cys Phe Pro Gly Thr Ser Leu Glu Asn Ile
    370                 375                 380

Tyr Ser Met Met Leu Thr Leu Ile Gly Gln Lys Leu Lys Asp Leu Gly
385                 390                 395                 400

Ile Met Lys Asn Ile Lys Glu Asn Asn Ala Phe Lys Ala Ala Arg Lys
                405                 410                 415

Tyr Cys Pro His His Val Gly His Tyr Leu Gly Met Asp Val His Asp
            420                 425                 430

Thr Pro Asp Met Pro Arg Ser Leu Pro Leu Gln Pro Gly Met Val Ile
        435                 440                 445

Thr Ile Glu Pro Gly Ile Tyr Ile Pro Glu Asp Asp Lys Asp Ala Pro
    450                 455                 460
```

-continued

```
Glu Lys Phe Arg Gly Leu Gly Val Arg Ile Glu Asp Asp Val Val Val
465                 470                 475                 480

Thr Gln Asp Ser Pro Leu Ile Leu Ser Ala Asp Cys Pro Lys Glu Met
                485                 490                 495

Asn Asp Ile Glu Gln Ile Cys Ser Gln Ala Ser
            500                 505


<210> SEQ ID NO 3
<211> LENGTH: 210
<212> TYPE: DNA
<213> ORGANISM: homo sapiens

<400> SEQUENCE: 3

atgccttggc tgctctcagc ccccaagctg gttcccgctg tagcaaacgt ccgcggcctc     60

tcaggatgta tgttgtgttc acagcgaagg tactcccttc agcctgtccc agaaaggagg    120

attccaaacc gatacttagg ccagcccagc ccctttacac acccacacct cctcagacca    180

gactcgaatt cctgctggga agtcggctga                                     210


<210> SEQ ID NO 4
<211> LENGTH: 69
<212> TYPE: PRT
<213> ORGANISM: homo sapiens

<400> SEQUENCE: 4

Met Pro Trp Leu Leu Ser Ala Pro Lys Leu Val Pro Ala Val Ala Asn
 1               5                  10                  15

Val Arg Gly Leu Ser Gly Cys Met Leu Cys Ser Gln Arg Arg Tyr Ser
            20                  25                  30

Leu Gln Pro Val Pro Glu Arg Arg Ile Pro Asn Arg Tyr Leu Gly Gln
        35                  40                  45

Pro Ser Pro Phe Thr His Pro His Leu Leu Arg Pro Asp Ser Asn Ser
    50                  55                  60

Cys Trp Glu Val Gly
65


<210> SEQ ID NO 5
<211> LENGTH: 873
<212> TYPE: DNA
<213> ORGANISM: homo sapiens

<400> SEQUENCE: 5

atgccttggc tgctctcagc ccccaagctg gttcccgctg tagcaaacgt ccgcggcctc     60

tcaggatgta tgttgtgttc acagcgaagg tactcccttc agcctgtccc agaaaggagg    120

attccaaacc gatacttagg ccagcccagc ccctttacac acccacacct cctcagacca    180

ggggaggtaa ctccaggact atctcaggtg gaatatgcac ttcgcagaca caaactaatg    240

tctctgatcc agaaggaagc tcaagggcag agtgggacag accagacagt ggttgtgctc    300

tccaacccta catactacat gagcaacgat attccctata ctttccacca agacaacaat    360

ttcctgtacc tatgtggatt ccaagagcct gatagcattc ttgtccttca gagcctccct    420

ggcaaacaat taccatcaca caaagccata ctttttgtgc ctcggcgaga tcccagtcga    480

gaactttggg atggtccgcg atctggcact gatggagcaa tagctctaac tggagtagac    540

gaagcctata cgctagaaga atttcaacat cttctaccaa aaatgaaagt gctcttgcca    600

gctcttcaaa aggaggtact gttctccaag aacgatccat gcatcacagc atcagaatca    660
```

-continued

```
cctgctgaga cgaacatggt ttggtatgac tggatgaggc cctcacatgc acagcttcac    720

tctgactata tgcagcccct gactgaggcc aaagccaaga gcaagaacaa ggttcggggt    780

gttcagcagc tgatacagcg cctccggctg atcaagtctc ctgcagaaat tgaacgaatg    840

cagattgctg ggaagctgac atcacaggta tga                                 873
```

```
<210> SEQ ID NO 6
<211> LENGTH: 290
<212> TYPE: PRT
<213> ORGANISM: homo sapiens

<400> SEQUENCE: 6

Met Pro Trp Leu Leu Ser Ala Pro Lys Leu Val Pro Ala Val Ala Asn
 1               5                  10                  15

Val Arg Gly Leu Ser Gly Cys Met Leu Cys Ser Gln Arg Arg Tyr Ser
            20                  25                  30

Leu Gln Pro Val Pro Glu Arg Arg Ile Pro Asn Arg Tyr Leu Gly Gln
        35                  40                  45

Pro Ser Pro Phe Thr His Pro His Leu Leu Arg Pro Gly Glu Val Thr
    50                  55                  60

Pro Gly Leu Ser Gln Val Glu Tyr Ala Leu Arg Arg His Lys Leu Met
65                  70                  75                  80

Ser Leu Ile Gln Lys Glu Ala Gln Gly Gln Ser Gly Thr Asp Gln Thr
                85                  90                  95

Val Val Val Leu Ser Asn Pro Thr Tyr Tyr Met Ser Asn Asp Ile Pro
            100                 105                 110

Tyr Thr Phe His Gln Asp Asn Asn Phe Leu Tyr Leu Cys Gly Phe Gln
        115                 120                 125

Glu Pro Asp Ser Ile Leu Val Leu Gln Ser Leu Pro Gly Lys Gln Leu
    130                 135                 140

Pro Ser His Lys Ala Ile Leu Phe Val Pro Arg Arg Asp Pro Ser Arg
145                 150                 155                 160

Glu Leu Trp Asp Gly Pro Arg Ser Gly Thr Asp Gly Ala Ile Ala Leu
                165                 170                 175

Thr Gly Val Asp Glu Ala Tyr Thr Leu Glu Glu Phe Gln His Leu Leu
            180                 185                 190

Pro Lys Met Lys Val Leu Leu Pro Ala Leu Gln Lys Glu Val Leu Phe
        195                 200                 205

Ser Lys Asn Asp Pro Cys Ile Thr Ala Ser Glu Ser Pro Ala Glu Thr
    210                 215                 220

Asn Met Val Trp Tyr Asp Trp Met Arg Pro Ser His Ala Gln Leu His
225                 230                 235                 240

Ser Asp Tyr Met Gln Pro Leu Thr Glu Ala Lys Ala Lys Ser Lys Asn
                245                 250                 255

Lys Val Arg Gly Val Gln Gln Leu Ile Gln Arg Leu Arg Leu Ile Lys
            260                 265                 270

Ser Pro Ala Glu Ile Glu Arg Met Gln Ile Ala Gly Lys Leu Thr Ser
        275                 280                 285

Gln Val
    290
```

```
<210> SEQ ID NO 7
<211> LENGTH: 798
<212> TYPE: DNA
<213> ORGANISM: homo sapiens
```

-continued

<400> SEQUENCE: 7

```
atgccttggc tgctctcagc ccccaagctg gttcccgctg tagcaaacgt ccgcggcctc     60
tcaggatgta tgttgtgttc acagcgaagg tactcccttc agcctgtccc agaaaggagg    120
attccaaacc gatacttagg ccagcccagc ccctttacac acccacacct cctcagacca    180
ggggaggtaa ctccaggact atctcaggtg gaatatgcac ttcgcagaca caaactaatg    240
tctctgatcc agaaggaagc tcaagggcag agtgggacag accagacagt ggttgtgctc    300
tccaacccta catactacat gagcaacgat attccctata ctttccacca agacaacaat    360
ttcctgtacc tatgtggatt ccaagagcct gatagcattc ttgtccttca gagcctccct    420
ggcaaacaat taccatcaca caaagccata ctttttgtgc ctcggcgaga tcccagtcga    480
gaactttggg atggtccgcg atctggcact gatggagcaa tagctctaac tggagtagac    540
gaagcctata cgctagaaga atttcaacat cttctaccaa aaatgaaagc tgagacgaac    600
atggtttggt atgactggat gaggccctca catgcacagc ttcactctga ctatatgcag    660
cccctgactg aggccaaagc caagagcaag aacaaggttc ggggtgttca gcagctgata    720
cagcgcctcc ggctgatcaa gtctcctgca gaaattgaac gaatgcagat tgctgggaag    780
ctgacatcac aggtatga                                                  798
```

<210> SEQ ID NO 8
<211> LENGTH: 265
<212> TYPE: PRT
<213> ORGANISM: homo sapiens

<400> SEQUENCE: 8

```
Met Pro Trp Leu Leu Ser Ala Pro Lys Leu Val Pro Ala Val Ala Asn
 1               5                  10                  15

Val Arg Gly Leu Ser Gly Cys Met Leu Cys Ser Gln Arg Arg Tyr Ser
            20                  25                  30

Leu Gln Pro Val Pro Glu Arg Arg Ile Pro Asn Arg Tyr Leu Gly Gln
        35                  40                  45

Pro Ser Pro Phe Thr His Pro His Leu Leu Arg Pro Gly Glu Val Thr
    50                  55                  60

Pro Gly Leu Ser Gln Val Glu Tyr Ala Leu Arg Arg His Lys Leu Met
65                  70                  75                  80

Ser Leu Ile Gln Lys Glu Ala Gln Gly Gln Ser Gly Thr Asp Gln Thr
                85                  90                  95

Val Val Val Leu Ser Asn Pro Thr Tyr Tyr Met Ser Asn Asp Ile Pro
            100                 105                 110

Tyr Thr Phe His Gln Asp Asn Asn Phe Leu Tyr Leu Cys Gly Phe Gln
        115                 120                 125

Glu Pro Asp Ser Ile Leu Val Leu Gln Ser Leu Pro Gly Lys Gln Leu
    130                 135                 140

Pro Ser His Lys Ala Ile Leu Phe Val Pro Arg Arg Asp Pro Ser Arg
145                 150                 155                 160

Glu Leu Trp Asp Gly Pro Arg Ser Gly Thr Asp Gly Ala Ile Ala Leu
                165                 170                 175

Thr Gly Val Asp Glu Ala Tyr Thr Leu Glu Glu Phe Gln His Leu Leu
            180                 185                 190

Pro Lys Met Lys Ala Glu Thr Asn Met Val Trp Tyr Asp Trp Met Arg
        195                 200                 205

Pro Ser His Ala Gln Leu His Ser Asp Tyr Met Gln Pro Leu Thr Glu
    210                 215                 220
```

```
Ala Lys Ala Lys Ser Lys Asn Lys Val Arg Gly Val Gln Gln Leu Ile
225                 230                 235                 240

Gln Arg Leu Arg Leu Ile Lys Ser Pro Ala Glu Ile Glu Arg Met Gln
                245                 250                 255

Ile Ala Gly Lys Leu Thr Ser Gln Val
            260                 265


<210> SEQ ID NO 9
<211> LENGTH: 636
<212> TYPE: DNA
<213> ORGANISM: homo sapiens

<400> SEQUENCE: 9

atgtctctga tccagaagga agctcaaggg cagagtggga cagaccagac agtggttgtg      60

ctctccaacc ctacatacta catgagcaac gatattccct atactttcca ccaagacaac     120

aatttcctgt acctatgtgg attccaagag cctgatagca ttcttgtcct tcagagcctc     180

cctggcaaac aattaccatc acacaaagcc atactttttg tgcctcggcg agatcccagt     240

cgagaacttt gggatggtcc gcgatctggc actgatggag caatagctct aactggagta     300

gacgaagcct atacgctaga agaatttcaa catcttctac caaaaatgaa agtgctcttg     360

ccagctcttc aaaaggaggt actgttctcc aagaacgatc catgcatcac agcatcagaa     420

tcacctgctg agacgaacat ggtttggtat gactggatga ggccctcaca tgcacagctt     480

cactctgact atatgcagcc cctgactgag gccaaagcca agagcaagaa caaggttcgg     540

ggtgttcagc agctgataca gcgcctccgg ctgatcaagt ctcctgcaga aattgaacga     600

atgcagattg ctgggaagct gacatcacag gtatga                               636


<210> SEQ ID NO 10
<211> LENGTH: 211
<212> TYPE: PRT
<213> ORGANISM: homo sapiens

<400> SEQUENCE: 10

Met Ser Leu Ile Gln Lys Glu Ala Gln Gly Gln Ser Gly Thr Asp Gln
 1               5                  10                  15

Thr Val Val Val Leu Ser Asn Pro Thr Tyr Tyr Met Ser Asn Asp Ile
            20                  25                  30

Pro Tyr Thr Phe His Gln Asp Asn Asn Phe Leu Tyr Leu Cys Gly Phe
        35                  40                  45

Gln Glu Pro Asp Ser Ile Leu Val Leu Gln Ser Leu Pro Gly Lys Gln
    50                  55                  60

Leu Pro Ser His Lys Ala Ile Leu Phe Val Pro Arg Arg Asp Pro Ser
65                  70                  75                  80

Arg Glu Leu Trp Asp Gly Pro Arg Ser Gly Thr Asp Gly Ala Ile Ala
                85                  90                  95

Leu Thr Gly Val Asp Glu Ala Tyr Thr Leu Glu Glu Phe Gln His Leu
            100                 105                 110

Leu Pro Lys Met Lys Val Leu Leu Pro Ala Leu Gln Lys Glu Val Leu
        115                 120                 125

Phe Ser Lys Asn Asp Pro Cys Ile Thr Ala Ser Glu Ser Pro Ala Glu
    130                 135                 140

Thr Asn Met Val Trp Tyr Asp Trp Met Arg Pro Ser His Ala Gln Leu
145                 150                 155                 160

His Ser Asp Tyr Met Gln Pro Leu Thr Glu Ala Lys Ala Lys Ser Lys
```

-continued

```
            165                 170                 175

Asn Lys Val Arg Gly Val Gln Gln Leu Ile Gln Arg Leu Arg Leu Ile
            180                 185                 190

Lys Ser Pro Ala Glu Ile Glu Arg Met Gln Ile Ala Gly Lys Leu Thr
        195                 200                 205

Ser Gln Val
    210


<210> SEQ ID NO 11
<211> LENGTH: 804
<212> TYPE: DNA
<213> ORGANISM: homo sapiens

<400> SEQUENCE: 11

atgttgtgtt cacagcgaag gtactccctt cagcctgtcc cagaaaggag gattccaaac     60

cgatacttag gccagcccag cccctttaca cacccacacc tcctcagacc aggggaggta    120

actccaggac tatctcaggt ggaatatgca cttcgcagac acaaactaat gtctctgatc    180

cagaaggaag ctcaagggca gagtgggaca gaccagacag tggttgtgct ctccaaccct    240

acatactaca tgagcaacga tattccctat actttccacc aagacaacaa tttcctgtac    300

ctatgtggat tccaagagcc tgatagcatt cttgtccttc agagcctccc tggcaaacaa    360

ttaccatcac acaaagccat actttttgtg cctcggcgag atcccagtcg agaactttgg    420

gatggtccgc gatctggcac tgatggagca atagctctaa ctggagtaga cgaagcctat    480

acgctagaag aatttcaaca tcttctacca aaaatgaaag tgctcttgcc agctcttcaa    540

aaggaggtac tgttctccaa gaacgatcca tgcatcacag catcagaatc acctgctgag    600

acgaacatgg tttggtatga ctggatgagg ccctcacatg cacagcttca ctctgactat    660

atgcagcccc tgactgaggc caaagccaag agcaagaaca aggttcgggg tgttcagcag    720

ctgatacagc gcctccggct gatcaagtct cctgcagaaa ttgaacgaat gcagattgct    780

gggaagctga catcacaggt atga                                          804


<210> SEQ ID NO 12
<211> LENGTH: 267
<212> TYPE: PRT
<213> ORGANISM: homo sapiens

<400> SEQUENCE: 12

Met Leu Cys Ser Gln Arg Arg Tyr Ser Leu Gln Pro Val Pro Glu Arg
 1               5                  10                  15

Arg Ile Pro Asn Arg Tyr Leu Gly Gln Pro Ser Pro Phe Thr His Pro
            20                  25                  30

His Leu Leu Arg Pro Gly Glu Val Thr Pro Gly Leu Ser Gln Val Glu
        35                  40                  45

Tyr Ala Leu Arg Arg His Lys Leu Met Ser Leu Ile Gln Lys Glu Ala
    50                  55                  60

Gln Gly Gln Ser Gly Thr Asp Gln Thr Val Val Val Leu Ser Asn Pro
65                  70                  75                  80

Thr Tyr Tyr Met Ser Asn Asp Ile Pro Tyr Thr Phe His Gln Asp Asn
                85                  90                  95

Asn Phe Leu Tyr Leu Cys Gly Phe Gln Glu Pro Asp Ser Ile Leu Val
            100                 105                 110

Leu Gln Ser Leu Pro Gly Lys Gln Leu Pro Ser His Lys Ala Ile Leu
        115                 120                 125
```

-continued

```
Phe Val Pro Arg Arg Asp Pro Ser Arg Glu Leu Trp Asp Gly Pro Arg
    130                 135                 140

Ser Gly Thr Asp Gly Ala Ile Ala Leu Thr Gly Val Asp Glu Ala Tyr
145                 150                 155                 160

Thr Leu Glu Glu Phe Gln His Leu Leu Pro Lys Met Lys Val Leu Leu
                165                 170                 175

Pro Ala Leu Gln Lys Glu Val Leu Phe Ser Lys Asn Asp Pro Cys Ile
            180                 185                 190

Thr Ala Ser Glu Ser Pro Ala Glu Thr Asn Met Val Trp Tyr Asp Trp
        195                 200                 205

Met Arg Pro Ser His Ala Gln Leu His Ser Asp Tyr Met Gln Pro Leu
    210                 215                 220

Thr Glu Ala Lys Ala Lys Ser Lys Asn Lys Val Arg Gly Val Gln Gln
225                 230                 235                 240

Leu Ile Gln Arg Leu Arg Leu Ile Lys Ser Pro Ala Glu Ile Glu Arg
                245                 250                 255

Met Gln Ile Ala Gly Lys Leu Thr Ser Gln Val
            260                 265


<210> SEQ ID NO 13
<211> LENGTH: 561
<212> TYPE: DNA
<213> ORGANISM: homo sapiens

<400> SEQUENCE: 13

atgtctctga tccagaagga agctcaaggg cagagtggga cagaccagac agtggttgtg      60

ctctccaacc ctacatacta catgagcaac gatattccct atactttcca ccaagacaac     120

aatttcctgt acctatgtgg attccaagag cctgatagca ttcttgtcct tcagagcctc     180

cctggcaaac aattaccatc acacaaagcc atactttttg tgcctcggcg agatcccagt     240

cgagaacttt gggatggtcc gcgatctggc actgatggag caatagctct aactggagta     300

gacgaagcct atacgctaga agaatttcaa catcttctac caaaaatgaa agctgagacg     360

aacatggttt ggtatgactg gatgaggccc tcacatgcac agcttcactc tgactatatg     420

cagcccctga ctgaggccaa agccaagagc aagaacaagg ttcggggtgt tcagcagctg     480

atacagcgcc tccggctgat caagtctcct gcagaaattg aacgaatgca gattgctggg     540

aagctgacat cacaggtatg a                                               561


<210> SEQ ID NO 14
<211> LENGTH: 186
<212> TYPE: PRT
<213> ORGANISM: homo sapiens

<400> SEQUENCE: 14

Met Ser Leu Ile Gln Lys Glu Ala Gln Gly Gln Ser Gly Thr Asp Gln
 1               5                  10                  15

Thr Val Val Val Leu Ser Asn Pro Thr Tyr Tyr Met Ser Asn Asp Ile
            20                  25                  30

Pro Tyr Thr Phe His Gln Asp Asn Asn Phe Leu Tyr Leu Cys Gly Phe
        35                  40                  45

Gln Glu Pro Asp Ser Ile Leu Val Leu Gln Ser Leu Pro Gly Lys Gln
    50                  55                  60

Leu Pro Ser His Lys Ala Ile Leu Phe Val Pro Arg Arg Asp Pro Ser
65                  70                  75                  80

Arg Glu Leu Trp Asp Gly Pro Arg Ser Gly Thr Asp Gly Ala Ile Ala
```

-continued

```
                85                  90                  95

Leu Thr Gly Val Asp Glu Ala Tyr Thr Leu Glu Glu Phe Gln His Leu
            100                 105                 110

Leu Pro Lys Met Lys Ala Glu Thr Asn Met Val Trp Tyr Asp Trp Met
        115                 120                 125

Arg Pro Ser His Ala Gln Leu His Ser Asp Tyr Met Gln Pro Leu Thr
    130                 135                 140

Glu Ala Lys Ala Lys Ser Lys Asn Lys Val Arg Gly Val Gln Gln Leu
145                 150                 155                 160

Ile Gln Arg Leu Arg Leu Ile Lys Ser Pro Ala Glu Ile Glu Arg Met
                165                 170                 175

Gln Ile Ala Gly Lys Leu Thr Ser Gln Val
            180                 185


<210> SEQ ID NO 15
<211> LENGTH: 729
<212> TYPE: DNA
<213> ORGANISM: homo sapiens

<400> SEQUENCE: 15

atgttgtgtt cacagcgaag gtactccctt cagcctgtcc cagaaaggag gattccaaac      60

cgatacttag gccagcccag ccccttaca cacccacacc tcctcagacc aggggaggta      120

actccaggac tatctcaggt ggaatatgca cttcgcagac acaaactaat gtctctgatc     180

cagaaggaag ctcaagggca gagtgggaca gaccagacag tggttgtgct ctccaaccct     240

acatactaca tgagcaacga tattccctat actttccacc aagacaacaa tttcctgtac     300

ctatgtggat tccaagagcc tgatagcatt cttgtccttc agagcctccc tggcaaacaa     360

ttaccatcac acaaagccat actttttgtg cctcggcgag atcccagtcg agaactttgg     420

gatggtccgc gatctggcac tgatggagca atagctctaa ctggagtaga cgaagcctat     480

acgctagaag aatttcaaca tcttctacca aaaatgaaag ctgagacgaa catggtttgg     540

tatgactgga tgaggccctc acatgcacag cttcactctg actatatgca gcccctgact     600

gaggccaaag ccaagagcaa gaacaaggtt cggggtgttc agcagctgat acagcgcctc     660

cggctgatca agtctcctgc agaaattgaa cgaatgcaga ttgctgggaa gctgacatca     720

caggtatga                                                            729


<210> SEQ ID NO 16
<211> LENGTH: 242
<212> TYPE: PRT
<213> ORGANISM: homo sapiens

<400> SEQUENCE: 16

Met Leu Cys Ser Gln Arg Arg Tyr Ser Leu Gln Pro Val Pro Glu Arg
 1               5                  10                  15

Arg Ile Pro Asn Arg Tyr Leu Gly Gln Pro Ser Pro Phe Thr His Pro
            20                  25                  30

His Leu Leu Arg Pro Gly Glu Val Thr Pro Gly Leu Ser Gln Val Glu
        35                  40                  45

Tyr Ala Leu Arg Arg His Lys Leu Met Ser Leu Ile Gln Lys Glu Ala
    50                  55                  60

Gln Gly Gln Ser Gly Thr Asp Gln Thr Val Val Val Leu Ser Asn Pro
65                  70                  75                  80

Thr Tyr Tyr Met Ser Asn Asp Ile Pro Tyr Thr Phe His Gln Asp Asn
                85                  90                  95
```

-continued

```
Asn Phe Leu Tyr Leu Cys Gly Phe Gln Glu Pro Asp Ser Ile Leu Val
            100                 105                 110

Leu Gln Ser Leu Pro Gly Lys Gln Leu Pro Ser His Lys Ala Ile Leu
        115                 120                 125

Phe Val Pro Arg Arg Asp Pro Ser Arg Glu Leu Trp Asp Gly Pro Arg
    130                 135                 140

Ser Gly Thr Asp Gly Ala Ile Ala Leu Thr Gly Val Asp Glu Ala Tyr
145                 150                 155                 160

Thr Leu Glu Glu Phe Gln His Leu Leu Pro Lys Met Lys Ala Glu Thr
                165                 170                 175

Asn Met Val Trp Tyr Asp Trp Met Arg Pro Ser His Ala Gln Leu His
            180                 185                 190

Ser Asp Tyr Met Gln Pro Leu Thr Glu Ala Lys Ala Lys Ser Lys Asn
        195                 200                 205

Lys Val Arg Gly Val Gln Gln Leu Ile Gln Arg Leu Arg Leu Ile Lys
    210                 215                 220

Ser Pro Ala Glu Ile Glu Arg Met Gln Ile Ala Gly Lys Leu Thr Ser
225                 230                 235                 240

Gln Val


<210> SEQ ID NO 17
<211> LENGTH: 1362
<212> TYPE: DNA
<213> ORGANISM: homo sapiens

<400> SEQUENCE: 17

atgtctctga tccagaagga agctcaaggg cagagtggga cagaccagac agtggttgtg     60

ctctccaacc ctacatacta catgagcaac gatattccct atactttcca ccaagacaac    120

aatttcctgt acctatgtgg attccaagag cctgatagca ttcttgtcct tcagagcctc    180

cctggcaaac aattaccatc acacaaagcc atactttttg tgcctcggcg agatcccagt    240

cgagaacttt gggatggtcc gcgatctggc actgatggag caatagctct aactggagta    300

gacgaagcct atacgctaga agaatttcaa catcttctac caaaaatgaa agtgctcttg    360

ccagctcttc aaaaggaggt actgttctcc aagaacgatc catgcatcac agcatcagaa    420

tcacctgctg agacgaacat ggtttggtat gactggatga ggccctcaca tgcacagctt    480

cactctgact atatgcagcc cctgactgag gccaaagcca agagcaagaa caaggttcgg    540

ggtgttcagc agctgataca gcgcctccgg ctgatcaagt ctcctgcaga aattgaacga    600

atgcagattg ctgggaagct gacatcacag gctttcatag aaaccatgtt caccagtaaa    660

gcccctgtgg aagaagcctt tctttatgct aagtttgaat ttgaatgccg ggctcgtggc    720

gcagacattt tagcctatcc acctgtggtg gctggtggta atcggtcaaa cactttgcac    780

tatgtgaaaa ataatcaact catcaaggat ggggaaatgg tgcttctgga tggaggttgt    840

gagtcttcct gctatgtgag tgacatcaca cgtacgtggc cagtcaatgg caggttcacc    900

gcacctcagg cagaactcta tgaagccgtt ctagagatcc aaagagattg tttggccctc    960

tgcttccctg ggacaagctt ggagaacatc tacagcatga tgctgaccct gataggacag   1020

aagcttaaag acttggggat catgaagaac attaaggaaa ataatgcctt caaggctgct   1080

cgaaaatact gtcctcatca tgttggccac tacctcggga tggatgtcca tgacactcca   1140

gacatgcccc gttccctccc tctgcagcct gggatggtaa tcacaattga gcccggcatt   1200

tatattccag aggatgacaa agatgcccca gagaagtttc ggggtcttgg tgtacgaatt   1260
```

-continued

```
gaggatgatg tagtggtgac tcaggactca cctctcatcc tttctgcaga ctgtcccaaa   1320

gagatgaatg acattgaaca gatatgcagc caggcttctt ga                      1362


<210> SEQ ID NO 18
<211> LENGTH: 453
<212> TYPE: PRT
<213> ORGANISM: homo sapiens

<400> SEQUENCE: 18

Met Ser Leu Ile Gln Lys Glu Ala Gln Gly Gln Ser Gly Thr Asp Gln
 1               5                  10                  15

Thr Val Val Val Leu Ser Asn Pro Thr Tyr Tyr Met Ser Asn Asp Ile
            20                  25                  30

Pro Tyr Thr Phe His Gln Asp Asn Asn Phe Leu Tyr Leu Cys Gly Phe
        35                  40                  45

Gln Glu Pro Asp Ser Ile Leu Val Leu Gln Ser Leu Pro Gly Lys Gln
    50                  55                  60

Leu Pro Ser His Lys Ala Ile Leu Phe Val Pro Arg Arg Asp Pro Ser
65                  70                  75                  80

Arg Glu Leu Trp Asp Gly Pro Arg Ser Gly Thr Asp Gly Ala Ile Ala
                85                  90                  95

Leu Thr Gly Val Asp Glu Ala Tyr Thr Leu Glu Glu Phe Gln His Leu
            100                 105                 110

Leu Pro Lys Met Lys Val Leu Leu Pro Ala Leu Gln Lys Glu Val Leu
        115                 120                 125

Phe Ser Lys Asn Asp Pro Cys Ile Thr Ala Ser Glu Ser Pro Ala Glu
    130                 135                 140

Thr Asn Met Val Trp Tyr Asp Trp Met Arg Pro Ser His Ala Gln Leu
145                 150                 155                 160

His Ser Asp Tyr Met Gln Pro Leu Thr Glu Ala Lys Ala Lys Ser Lys
                165                 170                 175

Asn Lys Val Arg Gly Val Gln Gln Leu Ile Gln Arg Leu Arg Leu Ile
            180                 185                 190

Lys Ser Pro Ala Glu Ile Glu Arg Met Gln Ile Ala Gly Lys Leu Thr
        195                 200                 205

Ser Gln Ala Phe Ile Glu Thr Met Phe Thr Ser Lys Ala Pro Val Glu
    210                 215                 220

Glu Ala Phe Leu Tyr Ala Lys Phe Glu Phe Glu Cys Arg Ala Arg Gly
225                 230                 235                 240

Ala Asp Ile Leu Ala Tyr Pro Pro Val Val Ala Gly Gly Asn Arg Ser
                245                 250                 255

Asn Thr Leu His Tyr Val Lys Asn Asn Gln Leu Ile Lys Asp Gly Glu
            260                 265                 270

Met Val Leu Leu Asp Gly Gly Cys Glu Ser Ser Cys Tyr Val Ser Asp
        275                 280                 285

Ile Thr Arg Thr Trp Pro Val Asn Gly Arg Phe Thr Ala Pro Gln Ala
    290                 295                 300

Glu Leu Tyr Glu Ala Val Leu Glu Ile Gln Arg Asp Cys Leu Ala Leu
305                 310                 315                 320

Cys Phe Pro Gly Thr Ser Leu Glu Asn Ile Tyr Ser Met Met Leu Thr
                325                 330                 335

Leu Ile Gly Gln Lys Leu Lys Asp Leu Gly Ile Met Lys Asn Ile Lys
            340                 345                 350
```

-continued

```
Glu Asn Asn Ala Phe Lys Ala Ala Arg Lys Tyr Cys Pro His His Val
        355                 360                 365

Gly His Tyr Leu Gly Met Asp Val His Asp Thr Pro Asp Met Pro Arg
    370                 375                 380

Ser Leu Pro Leu Gln Pro Gly Met Val Ile Thr Ile Glu Pro Gly Ile
385                 390                 395                 400

Tyr Ile Pro Glu Asp Asp Lys Asp Ala Pro Glu Lys Phe Arg Gly Leu
                405                 410                 415

Gly Val Arg Ile Glu Asp Asp Val Val Val Thr Gln Asp Ser Pro Leu
            420                 425                 430

Ile Leu Ser Ala Asp Cys Pro Lys Glu Met Asn Asp Ile Glu Gln Ile
        435                 440                 445

Cys Ser Gln Ala Ser
    450


<210> SEQ ID NO 19
<211> LENGTH: 1599
<212> TYPE: DNA
<213> ORGANISM: homo sapiens

<400> SEQUENCE: 19

atgccttggc tgctctcagc ccccaagctg gttcccgctg tagcaaacgt ccgcggcctc      60

tcaggatgta tgttgtgttc acagcgaagg tactcccttc agcctgtccc agaaaggagg     120

attccaaacc gatacttagg ccagcccagc ccctttacac acccacacct cctcagacca     180

ggggaggtaa ctccaggact atctcaggtg gaatatgcac ttcgcagaca caaactaatg     240

tctctgatcc agaaggaagc tcaagggcag agtgggacag accagacagt ggttgtgctc     300

tccaacccta catactacat gagcaacgat attccctata ctttccacca agacaacaat     360

ttcctgtacc tatgtggatt ccaagagcct gatagcattc ttgtccttca gagcctccct     420

ggcaaacaat taccatcaca caaagccata ctttttgtgc ctcggcgaga tcccagtcga     480

gaactttggg atggtccgcg atctggcact gatggagcaa tagctctaac tggagtagac     540

gaagcctata cgctagaaga atttcaacat cttctaccaa aaatgaaagt gctcttgcca     600

gctcttcaaa aggaggtact gttctccaag aacgatccat gcatcacagc atcagaatca     660

cctgctgaga cgaacatggt ttggtatgac tggatgaggc cctcacatgc acagcttcac     720

tctgactata tgcagcccct gactgaggcc aaagccaaga gcaagaacaa ggttcggggt     780

gttcagcagc tgatacagcg cctccggctg atcaagtctc ctgcagaaat tgaacgaatg     840

cagattgctg ggaagctgac atcacaggct ttcatagaaa ccatgttcac cagtaaagcc     900

cctgtggaag aagcctttct ttatgctaag tttgaatttg aatgccgggc tcgtggcgca     960

gacattttag cctatccacc tgtggtggct ggtggtaatc ggtcaaacac tttgcactat    1020

gtgaaaaata atcaactcat caaggatggg gaaatggtgc ttctggatgg aggttgtgag    1080

tcttcctgct atgtgagtga catcacacgt acgtggccag tcaatggcag gttcaccgca    1140

cctcaggcag aactctatga agccgttcta gagatccaaa gagattgttt ggccctctgc    1200

ttccctggga caagcttgga gaacatctac agcatgatgc tgaccctgat aggacagaag    1260

cttaaagact tggggatcat gaagaacatt aaggaaaata atgccttcaa ggctgctcga    1320

aaatactgtc ctcatcatgt tggccactac ctcgggatgg atgtccatga cactccagac    1380

atgccccgtt ccctccctct gcagcctggg atggtaatca caattgagcc cggcatttat    1440

attccagagg atgacaaaga tgccccagag aagtttcggg gtcttggtgt acgaattgag    1500
```

-continued

```
gatgatgtag tggtgactca ggactcacct ctcatccttt ctgcagactg tcccaaagag   1560

atgaatgaca ttgaacagat atgcagccag gcttcttga                          1599


<210> SEQ ID NO 20
<211> LENGTH: 532
<212> TYPE: PRT
<213> ORGANISM: homo sapiens

<400> SEQUENCE: 20

Met Pro Trp Leu Leu Ser Ala Pro Lys Leu Val Pro Ala Val Ala Asn
 1               5                  10                  15

Val Arg Gly Leu Ser Gly Cys Met Leu Cys Ser Gln Arg Arg Tyr Ser
            20                  25                  30

Leu Gln Pro Val Pro Glu Arg Arg Ile Pro Asn Arg Tyr Leu Gly Gln
        35                  40                  45

Pro Ser Pro Phe Thr His Pro His Leu Leu Arg Pro Gly Glu Val Thr
    50                  55                  60

Pro Gly Leu Ser Gln Val Glu Tyr Ala Leu Arg Arg His Lys Leu Met
65                  70                  75                  80

Ser Leu Ile Gln Lys Glu Ala Gln Gly Gln Ser Gly Thr Asp Gln Thr
                85                  90                  95

Val Val Val Leu Ser Asn Pro Thr Tyr Tyr Met Ser Asn Asp Ile Pro
            100                 105                 110

Tyr Thr Phe His Gln Asp Asn Asn Phe Leu Tyr Leu Cys Gly Phe Gln
        115                 120                 125

Glu Pro Asp Ser Ile Leu Val Leu Gln Ser Leu Pro Gly Lys Gln Leu
    130                 135                 140

Pro Ser His Lys Ala Ile Leu Phe Val Pro Arg Arg Asp Pro Ser Arg
145                 150                 155                 160

Glu Leu Trp Asp Gly Pro Arg Ser Gly Thr Asp Gly Ala Ile Ala Leu
                165                 170                 175

Thr Gly Val Asp Glu Ala Tyr Thr Leu Glu Glu Phe Gln His Leu Leu
            180                 185                 190

Pro Lys Met Lys Val Leu Leu Pro Ala Leu Gln Lys Glu Val Leu Phe
        195                 200                 205

Ser Lys Asn Asp Pro Cys Ile Thr Ala Ser Glu Ser Pro Ala Glu Thr
    210                 215                 220

Asn Met Val Trp Tyr Asp Trp Met Arg Pro Ser His Ala Gln Leu His
225                 230                 235                 240

Ser Asp Tyr Met Gln Pro Leu Thr Glu Ala Lys Ala Lys Ser Lys Asn
                245                 250                 255

Lys Val Arg Gly Val Gln Gln Leu Ile Gln Arg Leu Arg Leu Ile Lys
            260                 265                 270

Ser Pro Ala Glu Ile Glu Arg Met Gln Ile Ala Gly Lys Leu Thr Ser
        275                 280                 285

Gln Ala Phe Ile Glu Thr Met Phe Thr Ser Lys Ala Pro Val Glu Glu
    290                 295                 300

Ala Phe Leu Tyr Ala Lys Phe Glu Phe Glu Cys Arg Ala Arg Gly Ala
305                 310                 315                 320

Asp Ile Leu Ala Tyr Pro Pro Val Val Ala Gly Gly Asn Arg Ser Asn
                325                 330                 335

Thr Leu His Tyr Val Lys Asn Asn Gln Leu Ile Lys Asp Gly Glu Met
            340                 345                 350

Val Leu Leu Asp Gly Gly Cys Glu Ser Ser Cys Tyr Val Ser Asp Ile
```

-continued

```
        355                 360                 365

Thr Arg Thr Trp Pro Val Asn Gly Arg Phe Thr Ala Pro Gln Ala Glu
    370                 375                 380

Leu Tyr Glu Ala Val Leu Glu Ile Gln Arg Asp Cys Leu Ala Leu Cys
385                 390                 395                 400

Phe Pro Gly Thr Ser Leu Glu Asn Ile Tyr Ser Met Met Leu Thr Leu
                405                 410                 415

Ile Gly Gln Lys Leu Lys Asp Leu Gly Ile Met Lys Asn Ile Lys Glu
            420                 425                 430

Asn Asn Ala Phe Lys Ala Ala Arg Lys Tyr Cys Pro His His Val Gly
        435                 440                 445

His Tyr Leu Gly Met Asp Val His Asp Thr Pro Asp Met Pro Arg Ser
    450                 455                 460

Leu Pro Leu Gln Pro Gly Met Val Ile Thr Ile Glu Pro Gly Ile Tyr
465                 470                 475                 480

Ile Pro Glu Asp Asp Lys Asp Ala Pro Glu Lys Phe Arg Gly Leu Gly
                485                 490                 495

Val Arg Ile Glu Asp Asp Val Val Val Thr Gln Asp Ser Pro Leu Ile
            500                 505                 510

Leu Ser Ala Asp Cys Pro Lys Glu Met Asn Asp Ile Glu Gln Ile Cys
        515                 520                 525

Ser Gln Ala Ser
    530


<210> SEQ ID NO 21
<211> LENGTH: 1287
<212> TYPE: DNA
<213> ORGANISM: homo sapiens

<400> SEQUENCE: 21

atgtctctga tccagaagga agctcaaggg cagagtggga cagaccagac agtggttgtg      60

ctctccaacc ctacatacta catgagcaac gatattccct atactttcca ccaagacaac     120

aatttcctgt acctatgtgg attccaagag cctgatagca ttcttgtcct tcagagcctc     180

cctggcaaac aattaccatc acacaaagcc atactttttg tgcctcggcg agatcccagt     240

cgagaacttt gggatggtcc gcgatctggc actgatggag caatagctct aactggagta     300

gacgaagcct atacgctaga agaatttcaa catcttctac caaaaatgaa agctgagacg     360

aacatggttt ggtatgactg gatgaggccc tcacatgcac agcttcactc tgactatatg     420

cagcccctga ctgaggccaa agccaagagc aagaacaagg ttcggggtgt tcagcagctg     480

atacagcgcc tccggctgat caagtctcct gcagaaattg aacgaatgca gattgctggg     540

aagctgacat cacaggcttt catagaaacc atgttcacca gtaaagcccc tgtggaagaa     600

gcctttcttt atgctaagtt tgaatttgaa tgccgggctc gtggcgcaga cattttagcc     660

tatccacctg tggtggctgg tggtaatcgg tcaaacactt tgcactatgt gaaaaataat     720

caactcatca aggatgggga aatggtgctt ctggatggag gttgtgagtc ttcctgctat     780

gtgagtgaca tcacacgtac gtggccagtc aatggcaggt tcaccgcacc tcaggcagaa     840

ctctatgaag ccgttctaga gatccaaaga gattgtttgg ccctctgctt ccctgggaca     900

agcttggaga acatctacag catgatgctg accctgatag gacagaagct taaagacttg     960

gggatcatga agaacattaa ggaaaataat gccttcaagg ctgctcgaaa atactgtcct    1020

catcatgttg gccactacct cgggatggat gtccatgaca ctccagacat gccccgttcc    1080
```

-continued

```
ctccctctgc agcctgggat ggtaatcaca attgagcccg gcatttatat tccagaggat   1140

gacaaagatg ccccagagaa gtttcggggt cttggtgtac gaattgagga tgatgtagtg   1200

gtgactcagg actcacctct catcctttct gcagactgtc ccaaagagat gaatgacatt   1260

gaacagatat gcagccaggc ttcttga                                       1287


<210> SEQ ID NO 22
<211> LENGTH: 428
<212> TYPE: PRT
<213> ORGANISM: homo sapiens

<400> SEQUENCE: 22

Met Ser Leu Ile Gln Lys Glu Ala Gln Gly Gln Ser Gly Thr Asp Gln
 1               5                  10                  15

Thr Val Val Val Leu Ser Asn Pro Thr Tyr Tyr Met Ser Asn Asp Ile
            20                  25                  30

Pro Tyr Thr Phe His Gln Asp Asn Asn Phe Leu Tyr Leu Cys Gly Phe
        35                  40                  45

Gln Glu Pro Asp Ser Ile Leu Val Leu Gln Ser Leu Pro Gly Lys Gln
    50                  55                  60

Leu Pro Ser His Lys Ala Ile Leu Phe Val Pro Arg Arg Asp Pro Ser
65                  70                  75                  80

Arg Glu Leu Trp Asp Gly Pro Arg Ser Gly Thr Asp Gly Ala Ile Ala
                85                  90                  95

Leu Thr Gly Val Asp Glu Ala Tyr Thr Leu Glu Glu Phe Gln His Leu
            100                 105                 110

Leu Pro Lys Met Lys Ala Glu Thr Asn Met Val Trp Tyr Asp Trp Met
        115                 120                 125

Arg Pro Ser His Ala Gln Leu His Ser Asp Tyr Met Gln Pro Leu Thr
    130                 135                 140

Glu Ala Lys Ala Lys Ser Lys Asn Lys Val Arg Gly Val Gln Gln Leu
145                 150                 155                 160

Ile Gln Arg Leu Arg Leu Ile Lys Ser Pro Ala Glu Ile Glu Arg Met
                165                 170                 175

Gln Ile Ala Gly Lys Leu Thr Ser Gln Ala Phe Ile Glu Thr Met Phe
            180                 185                 190

Thr Ser Lys Ala Pro Val Glu Glu Ala Phe Leu Tyr Ala Lys Phe Glu
        195                 200                 205

Phe Glu Cys Arg Ala Arg Gly Ala Asp Ile Leu Ala Tyr Pro Pro Val
    210                 215                 220

Val Ala Gly Gly Asn Arg Ser Asn Thr Leu His Tyr Val Lys Asn Asn
225                 230                 235                 240

Gln Leu Ile Lys Asp Gly Glu Met Val Leu Leu Asp Gly Gly Cys Glu
                245                 250                 255

Ser Ser Cys Tyr Val Ser Asp Ile Thr Arg Thr Trp Pro Val Asn Gly
            260                 265                 270

Arg Phe Thr Ala Pro Gln Ala Glu Leu Tyr Glu Ala Val Leu Glu Ile
        275                 280                 285

Gln Arg Asp Cys Leu Ala Leu Cys Phe Pro Gly Thr Ser Leu Glu Asn
    290                 295                 300

Ile Tyr Ser Met Met Leu Thr Leu Ile Gly Gln Lys Leu Lys Asp Leu
305                 310                 315                 320

Gly Ile Met Lys Asn Ile Lys Glu Asn Asn Ala Phe Lys Ala Ala Arg
                325                 330                 335
```

-continued

```
Lys Tyr Cys Pro His His Val Gly His Tyr Leu Gly Met Asp Val His
            340                 345                 350

Asp Thr Pro Asp Met Pro Arg Ser Leu Pro Leu Gln Pro Gly Met Val
        355                 360                 365

Ile Thr Ile Glu Pro Gly Ile Tyr Ile Pro Glu Asp Asp Lys Asp Ala
    370                 375                 380

Pro Glu Lys Phe Arg Gly Leu Gly Val Arg Ile Glu Asp Asp Val Val
385                 390                 395                 400

Val Thr Gln Asp Ser Pro Leu Ile Leu Ser Ala Asp Cys Pro Lys Glu
                405                 410                 415

Met Asn Asp Ile Glu Gln Ile Cys Ser Gln Ala Ser
            420                 425


<210> SEQ ID NO 23
<211> LENGTH: 1530
<212> TYPE: DNA
<213> ORGANISM: homo sapiens

<400> SEQUENCE: 23

atgttgtgtt cacagcgaag gtactccctt cagcctgtcc cagaaaggag gattccaaac      60

cgatacttag gccagcccag ccccttttaca cacccacacc tcctcagacc aggggaggta    120

actccaggac tatctcaggt ggaatatgca cttcgcagac acaaactaat gtctctgatc    180

cagaaggaag ctcaagggca gagtgggaca gaccagacag tggttgtgct ctccaaccct    240

acatactaca tgagcaacga tattccctat actttccacc aagacaacaa tttcctgtac    300

ctatgtggat tccaagagcc tgatagcatt cttgtccttc agagcctccc tggcaaacaa    360

ttaccatcac acaaagccat actttttgtg cctcggcgag atcccagtcg agaactttgg    420

gatggtccgc gatctggcac tgatggagca atagctctaa ctggagtaga cgaagcctat    480

acgctagaag aatttcaaca tcttctacca aaaatgaaag tgctcttgcc agctcttcaa    540

aaggaggtac tgttctccaa gaacgatcca tgcatcacag catcagaatc acctgctgag    600

acgaacatgg tttggtatga ctggatgagg ccctcacatg cacagcttca ctctgactat    660

atgcagcccc tgactgaggc caaagccaag agcaagaaca aggttcgggg tgttcagcag    720

ctgatacagc gcctccggct gatcaagtct cctgcagaaa ttgaacgaat gcagattgct    780

gggaagctga catcacaggc tttcatagaa accatgttca ccagtaaagc cctgtggaa     840

gaagcctttc tttatgctaa gtttgaattt gaatgccggg ctcgtggcgc agacatttta    900

gcctatccac ctgtggtggc tggtggtaat cggtcaaaca ctttgcacta tgtgaaaaat    960

aatcaactca tcaaggatgg ggaaatggtg cttctggatg gaggttgtga gtcttcctgc   1020

tatgtgagtg acatcacacg tacgtggcca gtcaatggca ggttcaccgc acctcaggca   1080

gaactctatg aagccgttct agagatccaa agagattgtt tggccctctg cttccctggg   1140

acaagcttgg agaacatcta cagcatgatg ctgaccctga taggacagaa gcttaaagac   1200

ttggggatca tgaagaacat taaggaaaat aatgccttca aggctgctcg aaaatactgt   1260

cctcatcatg ttggccacta cctcgggatg gatgtccatg acactccaga catgccccgt   1320

tccctccctc tgcagcctgg gatggtaatc acaattgagc ccggcattta tattccagag   1380

gatgacaaag atgccccaga gaagtttcgg ggtcttggtg tacgaattga ggatgatgta   1440

gtggtgactc aggactcacc tctcatcctt tctgcagact gtcccaaaga gatgaatgac   1500

attgaacaga tatgcagcca ggcttcttga                                     1530
```

-continued

```
<210> SEQ ID NO 24
<211> LENGTH: 509
<212> TYPE: PRT
<213> ORGANISM: homo sapiens

<400> SEQUENCE: 24

Met Leu Cys Ser Gln Arg Arg Tyr Ser Leu Gln Pro Val Pro Glu Arg
 1              5                   10                  15

Arg Ile Pro Asn Arg Tyr Leu Gly Gln Pro Ser Pro Phe Thr His Pro
            20                  25                  30

His Leu Leu Arg Pro Gly Glu Val Thr Pro Gly Leu Ser Gln Val Glu
        35                  40                  45

Tyr Ala Leu Arg Arg His Lys Leu Met Ser Leu Ile Gln Lys Glu Ala
    50                  55                  60

Gln Gly Gln Ser Gly Thr Asp Gln Thr Val Val Val Leu Ser Asn Pro
65                  70                  75                  80

Thr Tyr Tyr Met Ser Asn Asp Ile Pro Tyr Thr Phe His Gln Asp Asn
                85                  90                  95

Asn Phe Leu Tyr Leu Cys Gly Phe Gln Glu Pro Asp Ser Ile Leu Val
            100                 105                 110

Leu Gln Ser Leu Pro Gly Lys Gln Leu Pro Ser His Lys Ala Ile Leu
        115                 120                 125

Phe Val Pro Arg Arg Asp Pro Ser Arg Glu Leu Trp Asp Gly Pro Arg
    130                 135                 140

Ser Gly Thr Asp Gly Ala Ile Ala Leu Thr Gly Val Asp Glu Ala Tyr
145                 150                 155                 160

Thr Leu Glu Glu Phe Gln His Leu Leu Pro Lys Met Lys Val Leu Leu
                165                 170                 175

Pro Ala Leu Gln Lys Glu Val Leu Phe Ser Lys Asn Asp Pro Cys Ile
            180                 185                 190

Thr Ala Ser Glu Ser Pro Ala Glu Thr Asn Met Val Trp Tyr Asp Trp
        195                 200                 205

Met Arg Pro Ser His Ala Gln Leu His Ser Asp Tyr Met Gln Pro Leu
    210                 215                 220

Thr Glu Ala Lys Ala Lys Ser Lys Asn Lys Val Arg Gly Val Gln Gln
225                 230                 235                 240

Leu Ile Gln Arg Leu Arg Leu Ile Lys Ser Pro Ala Glu Ile Glu Arg
                245                 250                 255

Met Gln Ile Ala Gly Lys Leu Thr Ser Gln Ala Phe Ile Glu Thr Met
            260                 265                 270

Phe Thr Ser Lys Ala Pro Val Glu Glu Ala Phe Leu Tyr Ala Lys Phe
        275                 280                 285

Glu Phe Glu Cys Arg Ala Arg Gly Ala Asp Ile Leu Ala Tyr Pro Pro
    290                 295                 300

Val Val Ala Gly Gly Asn Arg Ser Asn Thr Leu His Tyr Val Lys Asn
305                 310                 315                 320

Asn Gln Leu Ile Lys Asp Gly Glu Met Val Leu Leu Asp Gly Gly Cys
                325                 330                 335

Glu Ser Ser Cys Tyr Val Ser Asp Ile Thr Arg Thr Trp Pro Val Asn
            340                 345                 350

Gly Arg Phe Thr Ala Pro Gln Ala Glu Leu Tyr Glu Ala Val Leu Glu
        355                 360                 365

Ile Gln Arg Asp Cys Leu Ala Leu Cys Phe Pro Gly Thr Ser Leu Glu
    370                 375                 380
```

-continued

```
Asn Ile Tyr Ser Met Met Leu Thr Leu Ile Gly Gln Lys Leu Lys Asp
385                 390                 395                 400

Leu Gly Ile Met Lys Asn Ile Lys Glu Asn Asn Ala Phe Lys Ala Ala
                405                 410                 415

Arg Lys Tyr Cys Pro His His Val Gly His Tyr Leu Gly Met Asp Val
            420                 425                 430

His Asp Thr Pro Asp Met Pro Arg Ser Leu Pro Leu Gln Pro Gly Met
        435                 440                 445

Val Ile Thr Ile Glu Pro Gly Ile Tyr Ile Pro Glu Asp Asp Lys Asp
    450                 455                 460

Ala Pro Glu Lys Phe Arg Gly Leu Gly Val Arg Ile Glu Asp Asp Val
465                 470                 475                 480

Val Val Thr Gln Asp Ser Pro Leu Ile Leu Ser Ala Asp Cys Pro Lys
                485                 490                 495

Glu Met Asn Asp Ile Glu Gln Ile Cys Ser Gln Ala Ser
            500                 505


<210> SEQ ID NO 25
<211> LENGTH: 1455
<212> TYPE: DNA
<213> ORGANISM: homo sapiens

<400> SEQUENCE: 25

atgttgtgtt cacagcgaag gtactccctt cagcctgtcc cagaaaggag gattccaaac     60

cgatacttag gccagcccag cccctttaca cacccacacc tcctcagacc aggggaggta    120

actccaggac tatctcaggt ggaatatgca cttcgcagac acaaactaat gtctctgatc    180

cagaaggaag ctcaagggca gagtgggaca gaccagacag tggttgtgct ctccaaccct    240

acatactaca tgagcaacga tattccctat actttccacc aagacaacaa tttcctgtac    300

ctatgtggat tccaagagcc tgatagcatt cttgtccttc agagcctccc tggcaaacaa    360

ttaccatcac acaaagccat actttttgtg cctcggcgag atcccagtcg agaactttgg    420

gatggtccgc gatctggcac tgatggagca atagctctaa ctggagtaga cgaagcctat    480

acgctagaag aatttcaaca tcttctacca aaaatgaaag ctgagacgaa catggtttgg    540

tatgactgga tgaggccctc acatgcacag cttcactctg actatatgca gcccctgact    600

gaggccaaag ccaagagcaa gaacaaggtt cggggtgttc agcagctgat acagcgcctc    660

cggctgatca agtctcctgc agaaattgaa cgaatgcaga ttgctgggaa gctgacatca    720

caggctttca tagaaaccat gttcaccagt aaagcccctg tggaagaagc ctttctttat    780

gctaagtttg aatttgaatg ccgggctcgt ggcgcagaca ttttagccta tccacctgtg    840

gtggctggtg gtaatcggtc aaacactttg cactatgtga aaaataatca actcatcaag    900

gatggggaaa tggtgcttct ggatggaggt tgtgagtctt cctgctatgt gagtgacatc    960

acacgtacgt ggccagtcaa tggcaggttc accgcacctc aggcagaact ctatgaagcc   1020

gttctagaga tccaaagaga ttgtttggcc ctctgcttcc ctgggacaag cttggagaac   1080

atctacagca tgatgctgac cctgatagga cagaagctta aagacttggg gatcatgaag   1140

aacattaagg aaaataatgc cttcaaggct gctcgaaaat actgtcctca tcatgttggc   1200

cactacctcg ggatggatgt ccatgacact ccagacatgc ccgttccct ccctctgcag    1260

cctgggatgg taatcacaat tgagcccggc atttatattc cagaggatga caaagatgcc   1320

ccagagaagt ttcggggtct tggtgtacga attgaggatg atgtagtggt gactcaggac   1380

tcacctctca tcctttctgc agactgtccc aaagagatga atgacattga acagatatgc   1440
```

```
agccaggctt cttga                                                        1455

<210> SEQ ID NO 26
<211> LENGTH: 484
<212> TYPE: PRT
<213> ORGANISM: homo sapiens

<400> SEQUENCE: 26

Met Leu Cys Ser Gln Arg Arg Tyr Ser Leu Gln Pro Val Pro Glu Arg
 1               5                  10                  15

Arg Ile Pro Asn Arg Tyr Leu Gly Gln Pro Ser Pro Phe Thr His Pro
            20                  25                  30

His Leu Leu Arg Pro Gly Glu Val Thr Pro Gly Leu Ser Gln Val Glu
        35                  40                  45

Tyr Ala Leu Arg Arg His Lys Leu Met Ser Leu Ile Gln Lys Glu Ala
    50                  55                  60

Gln Gly Gln Ser Gly Thr Asp Gln Thr Val Val Val Leu Ser Asn Pro
65                  70                  75                  80

Thr Tyr Tyr Met Ser Asn Asp Ile Pro Tyr Thr Phe His Gln Asp Asn
                85                  90                  95

Asn Phe Leu Tyr Leu Cys Gly Phe Gln Glu Pro Asp Ser Ile Leu Val
            100                 105                 110

Leu Gln Ser Leu Pro Gly Lys Gln Leu Pro Ser His Lys Ala Ile Leu
        115                 120                 125

Phe Val Pro Arg Arg Asp Pro Ser Arg Glu Leu Trp Asp Gly Pro Arg
    130                 135                 140

Ser Gly Thr Asp Gly Ala Ile Ala Leu Thr Gly Val Asp Glu Ala Tyr
145                 150                 155                 160

Thr Leu Glu Glu Phe Gln His Leu Leu Pro Lys Met Lys Ala Glu Thr
                165                 170                 175

Asn Met Val Trp Tyr Asp Trp Met Arg Pro Ser His Ala Gln Leu His
            180                 185                 190

Ser Asp Tyr Met Gln Pro Leu Thr Glu Ala Lys Ala Lys Ser Lys Asn
        195                 200                 205

Lys Val Arg Gly Val Gln Gln Leu Ile Gln Arg Leu Arg Leu Ile Lys
    210                 215                 220

Ser Pro Ala Glu Ile Glu Arg Met Gln Ile Ala Gly Lys Leu Thr Ser
225                 230                 235                 240

Gln Ala Phe Ile Glu Thr Met Phe Thr Ser Lys Ala Pro Val Glu Glu
                245                 250                 255

Ala Phe Leu Tyr Ala Lys Phe Glu Phe Glu Cys Arg Ala Arg Gly Ala
            260                 265                 270

Asp Ile Leu Ala Tyr Pro Pro Val Val Ala Gly Gly Asn Arg Ser Asn
        275                 280                 285

Thr Leu His Tyr Val Lys Asn Asn Gln Leu Ile Lys Asp Gly Glu Met
    290                 295                 300

Val Leu Leu Asp Gly Gly Cys Glu Ser Ser Cys Tyr Val Ser Asp Ile
305                 310                 315                 320

Thr Arg Thr Trp Pro Val Asn Gly Arg Phe Thr Ala Pro Gln Ala Glu
                325                 330                 335

Leu Tyr Glu Ala Val Leu Glu Ile Gln Arg Asp Cys Leu Ala Leu Cys
            340                 345                 350

Phe Pro Gly Thr Ser Leu Glu Asn Ile Tyr Ser Met Met Leu Thr Leu
        355                 360                 365
```

-continued

```
Ile Gly Gln Lys Leu Lys Asp Leu Gly Ile Met Lys Asn Ile Lys Glu
    370                 375                 380

Asn Asn Ala Phe Lys Ala Ala Arg Lys Tyr Cys Pro His His Val Gly
385                 390                 395                 400

His Tyr Leu Gly Met Asp Val His Asp Thr Pro Asp Met Pro Arg Ser
                405                 410                 415

Leu Pro Leu Gln Pro Gly Met Val Ile Thr Ile Glu Pro Gly Ile Tyr
            420                 425                 430

Ile Pro Glu Asp Asp Lys Asp Ala Pro Glu Lys Phe Arg Gly Leu Gly
        435                 440                 445

Val Arg Ile Glu Asp Asp Val Val Val Thr Gln Asp Ser Pro Leu Ile
    450                 455                 460

Leu Ser Ala Asp Cys Pro Lys Glu Met Asn Asp Ile Glu Gln Ile Cys
465                 470                 475                 480

Ser Gln Ala Ser


<210> SEQ ID NO 27
<211> LENGTH: 3208
<212> TYPE: DNA
<213> ORGANISM: homo sapiens

<400> SEQUENCE: 27

gcggccctgc aggcggttgc gttccccgtc gttaccctct ttctcttccc gacgcgtgag     60

ttaggccgta atgccttggc tgctctcagc ccccaagctg gttcccgctg tagcaaacgt    120

ccgcggcctc tcagtcctga atcctctgga ctgtttcccc tgtatgtttc cctggaagct    180

tcaggcagtg cctcataagc caatggaatc tgttgctaat agccacagca tatcccttgc    240

ataatatgac ctctagatta ctgcgcctta attgcttccc agctcttcta tgctttggtt    300

tagaaaaatg aagtactgac ttacgggtga agaaagtatt caaacagttg acatatttat    360

ttcagtcaag aaacagttca gagggagata caaacaagta acttagttac aatataatag    420

ttatgatgag aggaagtact ggatgctaaa caattatatg agagacagct caggctgggg    480

gtgtcaatga aagcctcttg gaggaagtag cctgatatgt taactttctg catgccagtg    540

aagacactat gtgtgcatga gtacgtgtgc acgagcgtgc atgtggagaa ggtgcaggag    600

gagagaaaga gaaatcacca atgcaacagc agcctactcc accagtgggt tagtgctgct    660

ggagggagat gaaaagatta ggaaggatgt atgttgtgtt cacagcgaag gtactccctt    720

cagcctgtcc cagaaaggag gattccaaac cgatacttag gccagcccag ccccttttaca   780

cacccacacc tcctcagacc agactcgaat tcctgctggg aagtcggctg aaactaagga    840

aatgcagctc accactgaaa cccacaagaa atcagagttt ttcaaagctg taaggggagg    900

taactccagg actatctcag gtggaatatg cacttcgcag acacaaacta atgtctctga    960

tccagaagga agctcaaggg cagagtggga cagaccagac agtggttgtg ctctccaacc   1020

ctacatacta catgagcaac gatattccct atactttcca ccaagacaac aatttcctgt   1080

acctatgtgg attccaagag cctgatagca ttcttgtcct tcagagcctc cctggcaaac   1140

aattaccatc acacaaagcc atactttttg tgcctcggcg agatcccagt cgagaacttt   1200

gggatggtcc gcgatctggc actgatggag caatagctct aactggagta gacgaagcct   1260

atacgctaga agaatttcaa catcttctac caaaaatgaa agtgctcttg ccagctcttc   1320

aaaaggaggt actgttctcc aagaacgatc catgcatcac agcatcagaa tcacctgctg   1380

agacgaacat ggtttggtat gactggatga ggccctcaca tgcacagctt cactctgact   1440
```

-continued

```
atatgcagcc cctgactgag gccaaagcca agagcaagaa caaggttcgg ggtgttcagc   1500
agctgataca gcgcctccgg ctgatcaagt ctcctgcaga aattgaacga atgcagattg   1560
ctgggaagct gacatcacag gtatgattcc tattgaaaag ttttttccag ccgggcgcgg   1620
tggctcacgc ctgtaatcca agcactttgg gaggccgagg caggtggatc atgaggtcag   1680
gagatcgaga ccatcctggc taacatggtg aaaccccgtc tctactaaaa aaacataaaa   1740
aattagccgg gcatggtggc gggctcctgt agtcccagct actcggtagg ctgaggcagg   1800
agaatggtgt gaacccggga ggcagagctt gcagtgagcc gagatcgggc cactgcactc   1860
cagcctggcg acagacgaga ttcatcttaa aaaaaaaaaa aaaaaaaact ttcatagaaa   1920
ccatgttcac cagtaaagcc cctgtggaag aagcctttct ttatgctaag tttgaatttg   1980
aatgccgggc tcgtggcgca gacattttag cctatccacc tgtggtggct ggtggtaatc   2040
ggtcaaacac tttgcactat gtgaaaaata atcaactcat caaggatggg gaaatggtgc   2100
ttctggatgg aggttgtgag tcttcctgct atgtgagtga catcacacgt acgtggccag   2160
tcaatggcag gttcaccgca cctcaggcag aactctatga agccgttcta gagatccaaa   2220
gagattgttt ggccctctgc ttccctggga caagcttgga gaacatctac agcatgatgc   2280
tgaccctgat aggacagaag cttaaagact tggggatcat gaagaacatt aaggaaaata   2340
atgccttcaa ggctgctcga aaatactgtc ctcatcatgt tggccactac ctcgggatgg   2400
atgtccatga cactccagac atgccccgtt ccctccctct gcagcctggg atggtaatca   2460
caattgagcc cggcatttat attccagagg atgacaaaga tgccccagag aagtttcggg   2520
gtcttggtgt acgaattgag gatgatgtag tggtgactca ggactcacct ctcatccttt   2580
ctgcagactg tcccaaagag atgaatgaca ttgaacagat atgcagccag gcttcttgac   2640
cttcactgcg gcccacatgc acctcaggtt caaaatgggt gtcttctggc agccctgcac   2700
gtgtgctttc tgagtgtctc tgtgtgtgca ttaatatatg cattccattt gggagcataa   2760
aaaaaaaaaa aaaaatggaa tgcagtagcc ctctgggcct gggatattgt ggttgataac   2820
tgtgccatct gcaggaacca cattatggat ctttgcatag aatgtcaagc taaccaggcg   2880
tccgctactt cagaagagtg tactgtcgca tggggagtct gtaaccatgc ttttcacttc   2940
cactgcatct ctcgctggct caaaacacga caggtgtgtc cattggacaa cagagagtgg   3000
gaattccaaa agtatgggca ctaggaaaag acttcttcca tcaagcttaa ttgttttgtt   3060
attcatttaa tgactttccc tgctgttacc taattacaaa ttggatggaa ctgtgttttt   3120
ttctgctttg ttttttcagt ttgctgtttc tgtagccata ttggattctg tgtcaaataa   3180
agtccagttg gattctggaa aaaaaaaa                                      3208
```